March 5, 1974 W. H. JESSEL, JR., ET AL Plant Pat. 3,506
CHRYSANTHEMUM PLANT
Filed July 7, 1972
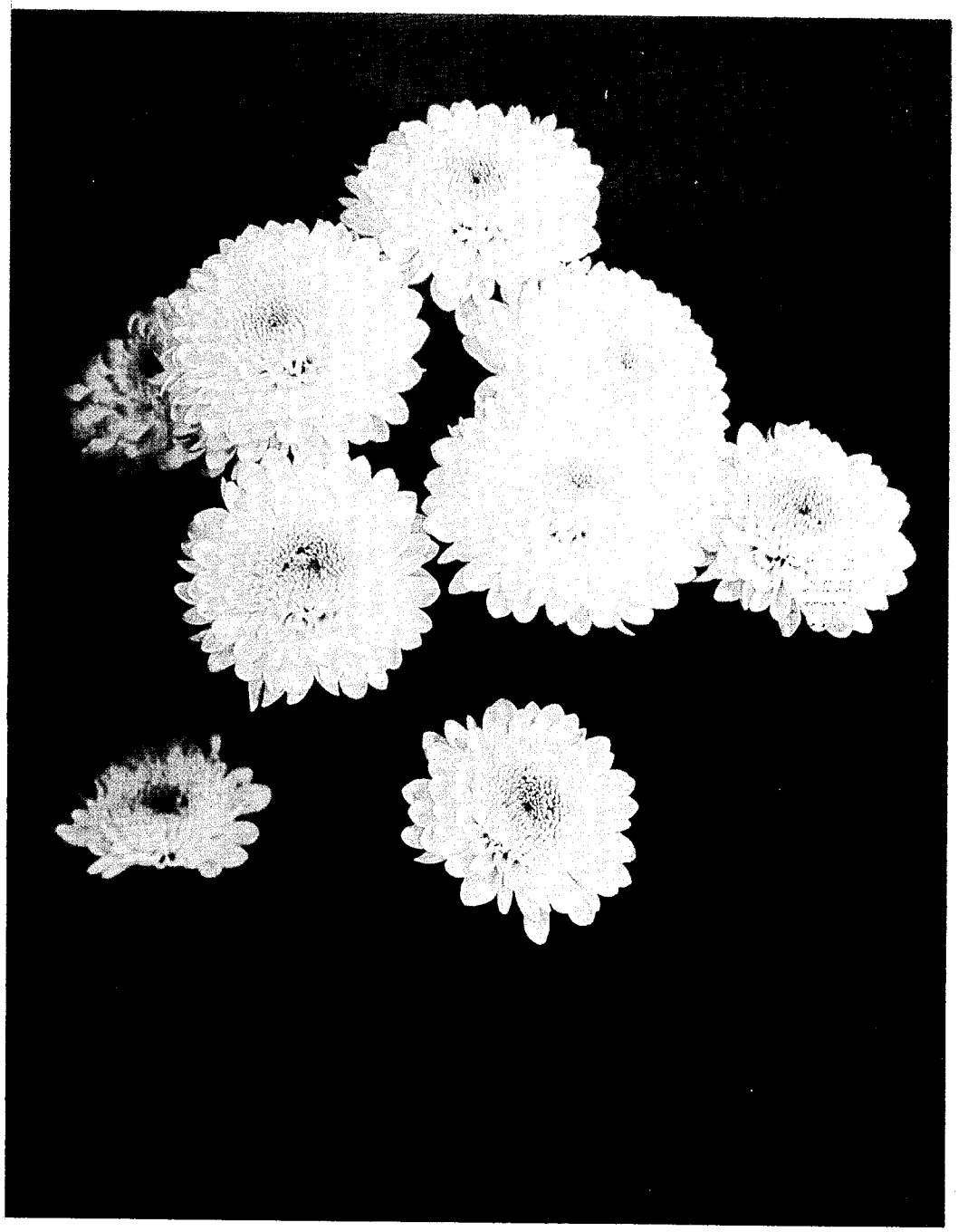

United States Patent Office

Plant Pat. 3,506

Patented Mar. 5, 1974

3,506
CHRYSANTHEMUM PLANT

Walter H. Jessel, Jr., Doylestown, and William E. Duffett, Akron, Ohio, assignors to Yoder Brothers, Inc., Barberton, Ohio

Filed July 7, 1972, Ser. No. 269,542
Int. Cl. A01h *5/00*
U.S. Cl. Plt.—78 1 Claim

The present invention comprises a new and distinct cultivar of chrysanthemum plant which is a sport of the cultivar named Symphony, disclosed and claimed in our pending application Ser. No. 264,305, filed June 19, 1972.

The new cultivar is similar in many respects to Symphony, having the same characteristics of:

(1) Recommended period of value.
(2) Foliage size, shape and texture.
(3) Flower form.

The new cultivar is distinguished from Symphony by the following characteristics when grown under comparable conditions:

(1) Its lemon yellow flower color.
(2) Approximately 2"–3" less vigor.
(3) Approximately 2–3 days later response.
(4) Flower approximately ¼" smaller in diameter.
(5) An average of one less flower per stem.
(6) Stem strength is slightly less.

The new cultivar was selected from a flowering block of the parent cultivar at Barberton, Ohio, and when asexually reproduced by cuttings by Yoder Brothers, Inc., at Barberton, Ohio, has been found to retain its distinctive characteristics through successive propagations.

The new cultivar when grown in the vicinity of Barberton, Ohio, has a response period of approximately 10 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States is from November through May; coastal California, November through May; and Florida, December through March.

The accompanying drawing, which comprises a color photograph, shows the unique characteristics of the new cultivar, the color being as nearly true as possible with color illustrations of this type.

In the following description, color references are made to the Munsell Color Book, 1963 edition, and color comparisons are made with the parent cultivar Symphony.

Botanical classification: *Chrysanthemum morifolium*

| | Harmony | Symphony |
|---|---|---|
| Bloom: | | |
| Size | 2¼" | 2½". |
| Fully expanded | 2½" | |
| Borne | Clusters of 7 on elongated pedicels | Clusters of 8 on elongated pedicels. |
| Stems | Strong | Very strong. |
| Form | Intermediate pom | |
| Permanence | 12–14 days | |
| Color | | |
| Center of flower | Yellow-green, 2.5GY7/10 | Yellow-green, 5GY8/6. |
| Base of petals | do | Yellow-green, 2.5GY8/8. |
| Inside of petals | Deep yellow, 5Y8.5/12 to yellow 7.5Y8.5/12 | Ivory white, 7.5Y9/4 to white, N9.5/. |
| Reverse of petals | Yellow, 7.5Y8.5/12. | White, No.5/. |
| Tonality from a distance | Yellow | Ivory white. |
| Discoloration | Yellow, 7.5Y8.5/12 | White, No.5/. |
| Petals: | | |
| Texture | Smooth | |
| Appearance & form | Open at base, deep rounded keel, tapering quickly to a blunt tip. | |
| Arrangement | Composite, whorled on a single receptacle | |
| Persistance | Resists shatter | |
| Fragrance | Typical chrysanthemum | |
| Reproductive organs: | | |
| Stamen, anthers | None | |
| Pollen | do | |
| Arrangement | Clustered in center of flower, if present | |
| Styles | Present ray florets | |
| Length | Short | |
| Ovaries | At the base of petal attached to receptacle | |
| Plant: | | |
| Form | Herbaceous | |
| Growth | Upright | |
| Height | Approximately 40"–42" when grown with 3–4 long day weeks and 13–14 weeks total crop time for the various seasons of the year as defined in the timetables of Yoder Brothers, Inc. | Approximately 42"–44" when grown with 3–4 long day weeks and 13–14 weeks total crop time for the various seasons of the year as defined in the timetables of Yoder Brothers, Inc. |
| Spread | None when grown single stem to moderate when pinched | |
| Foliage: | | |
| Top side | Dark green, 7.5GY3/4 | |
| Size | 4¾" long, 3" wide | |
| Quantity | Numerous | |
| Shape | Spatulate lobed | |
| Texture | Coarse | |
| Ribs & veins | Prominent | |
| Edge | Deeply indented | |
| Serration | Coarse | |
| Under side | Light green, 7.5GY5/4 | |
| Stipules | Prominent | |

We claim:

1. A new and distinct cultivar of chrysanthemum characterized particularly as to its uniqueness when compared to the parent cultivar Symphony by its lemon yellow flower color, approximately 2"–3" less vigor, 2–3 days later response, flowers which are approximately ¼" smaller in diameter, an average of one less flower per stem, and by its slightly less stem strength.

No references cited.

ROBERT E. BAGWILL, Primary Examiner